(12) United States Patent
Takeuchi

(10) Patent No.: US 6,183,502 B1
(45) Date of Patent: Feb. 6, 2001

(54) BLOOD FLOW BLOCKING METHOD AND WARMING APPARATUS

(75) Inventor: Yasuhito Takeuchi, Tokyo (JP)

(73) Assignee: GE Yokogawa Medical Systems, Limited, Tokyo (JP)

( * ) Notice: Under 35 U.S.C. 154(b), the term of this patent shall be extended for 0 days.

(21) Appl. No.: 09/204,579

(22) Filed: Dec. 3, 1998

(30) Foreign Application Priority Data

Jan. 1, 1998 (JP) .................................................. 10-030320
Oct. 16, 1998 (JP) .................................................. 10-331872

(51) Int. Cl.$^7$ ...................................................... A61F 7/12
(52) U.S. Cl. .............................. 607/113; 600/437; 604/22
(58) Field of Search ........................... 607/113; 600/462, 600/463, 437, 439; 604/22

(56) References Cited

U.S. PATENT DOCUMENTS

| | | |
|---|---|---|
| 3,615,972 | 10/1971 | Morehouse . |
| 4,364,392 | 12/1982 | Strother . |
| 4,586,512 * | 5/1986 | Do-Huu et al. . |
| 5,002,556 | 3/1991 | Terumo . |
| 5,368,031 | 11/1994 | Cline . |
| 5,490,840 | 2/1996 | Uzgiris . |
| 5,536,756 | 7/1996 | Kida . |
| 5,634,936 | 6/1997 | Linden . |
| 6,071,495 * | 6/2000 | Unger et al. ........................ 424/9.51 |

FOREIGN PATENT DOCUMENTS

| | | |
|---|---|---|
| 3504998 | 12/1985 | (DE) . |
| 375775 | 7/1990 | (EP) . |

* cited by examiner

Primary Examiner—Linda C. M. Dvorak
Assistant Examiner—Roy Gibson
(74) Attorney, Agent, or Firm—Moonray Kojima

(57) ABSTRACT

In order to choke a capillary vessel of a man with an expanded microballoon, a microballoon 1 is injected into a blood flow system of a man 12, and the microballoon 1 is expanded by warming a predefined region 13 in the man to increase the temperature of the region.

8 Claims, 2 Drawing Sheets

Pre-expanded State

Post-expanded State

US 6,183,502 B1

BLOOD FLOW BLOCKING METHOD AND WARMING APPARATUS

BACKGROUND OF THE INVENTION

The present invention relates to a method of blocking blood flow toward a target tissue such as cancerous tissue and a warming apparatus suitable for conducting the method, and more particularly, the invention relates to a blood flow blocking method and a warming apparatus for injecting into a blood flow system of a living body microballoons each having a shell made of a thermoplastic material and having a pressurized gas encapsulated within the shell, expanding the microballoons by increasing the temperature of the localized target tissue, and selectively blocking the blood flow of the body by choking capillary vessels with the expanded microballoons.

Examples of non-invasive therapy of cancer include a procedure wherein blood flow in blood vessels through which cancerous cells are nourished are blocked to necrotize the cancerous cells within a relatively short term.

A variety of techniques for blocking blood flow exist. Although these techniques are preferred rather than a technique which momentarily cauterizes the cancerous cells or a technique which slowly inhibits regeneration of the cancerous cells such as hyperthermia, a need is felt for an intermediate technique, like the techniques for blocking blood flow, which, in addition, allows a physician to instantly ascertain the result.

SUMMARY OF THE INVENTION

It is an object of the present invention to provide a blood flow blocking method and a warming apparatus which meet the above need.

In accordance with a first aspect, the present invention provides a blood flow blocking method which comprises the steps of: injecting microballoons into a blood flow system of a living body; expanding the microballoons by warming a predefined region of the body to increase the temperature of the region; and choking capillary vessels of the body with the expanded microballoons.

In accordance with a second aspect, the present invention provides a warming apparatus comprising means for warming a predefined region of a living body at which microballoons are injected into its blood flow system, the warming apparatus expanding the microballoons by increasing the temperature of the region.

In accordance with a third aspect, the present invention provides a warming apparatus comprising means for injecting microballoons into a blood flow system of a living body and means for warming a predefined region of the body, the warming apparatus expanding the microballoons by increasing the temperature of the region.

It is preferred that the microballoons as described regarding the above invention each have a shell made of a thermoplastic material within which a pressurized gas is encapsulated. The microballoons may be made solely of a biodegradable material or be made of a blend of a biodegradable material and a non-biodegradable material. Moreover, the microballoons may be made of a material blended with a heavy material, such as ferrite and magnetite, in order to enhance the warming effect.

In accordance with a fourth aspect, the present invention provides the blood flow blocking method of the first aspect, or the warming apparatus of the second or third aspect, wherein the softening point temperature of a material of the shell constituting the microballoon is higher than ordinary temperature of the body and is lower than the burn temperature of the body.

The softening point temperature is preferably slightly higher than the ordinary temperature of the body and is slightly lower than the burn temperature of the body, and is typically about 42° C.

In accordance with a fifth aspect, the present invention provides the blood flow blocking method of the first aspect, or the warming apparatus of the second, third or fourth aspect, wherein the warming means increases the temperature of the predefined region by transmitting a focused ultrasound toward the predefined region.

It is preferred that the transmission of the focused ultrasound be performed by an ultrasonic imaging system.

Further objects and advantages of the present invention will be apparent from the following description of the preferred embodiments of the invention as illustrated in the accompanying drawings.

DETAILED DESCRIPTION OF THE INVENTION

Preferred embodiments of the present invention will now be described in detail with reference to the accompanying drawings.

A microballoon for use in the present invention is no more than a few microns in size, and can be one that has been conventionally utilized as a contrast agent in ultrasonic imaging techniques. The shell of the microballoon is made of a thermoplastic and biocompatible material, and a low molecular weight hydrocarbon (e.g., nanobutane) is encapsulated within the shell. Although the microballoon does not expand at ordinary body temperature, it momentarily expands above its softening point temperature, making its diameter a few times larger and its volume 50 times larger, for example. That is, the shell of the microballoon softens over its softening point temperature and is enlarged by the pressure of a gas encapsulated therein, causing the microballoon to be expanded. The microballoon or microcapsule in which a pressurized gas is encapsulated is produced by a technique such as spray drying, in-site polymerization and in-site condensation. Of the produced microballoons or microcapsules, those which have a diameter of about 4–5 microns are selectively extracted.

The extracted microballoons or microcapsules are suspended in an appropriate buffer solution at a desired concentration, and the suspension is intravenously injected into an object living body such as a man or animal. After the microballoons or microcapsules pervade the tissue, a target region is heated by transmitting a focused ultrasound toward the region. For aiming the focused ultrasound, an imaging system in an ultrasonic imaging apparatus is employed. The least heating required to produce a temperature over the softening point temperature of the shell constituting the microballoon or microcapsule is sufficient, and such a temperature as to cause a burn to the tissue is not needed. While the microballoon or microcapsule for use in the present invention does not expand at, for example, 37° C., it momentarily expands at 42° C. from an initial diameter of 4 microns to a diameter as large as 15–20 microns. The microballoon or microcapsule having a diameter of 4 microns can unrestrictedly move through the capillary vessel, whereas the microballoon or microcapsule having a diameter of 15–20 microns chokes the capillary vessel, blocking the blood flow beyond the choked position.

Figure 1:
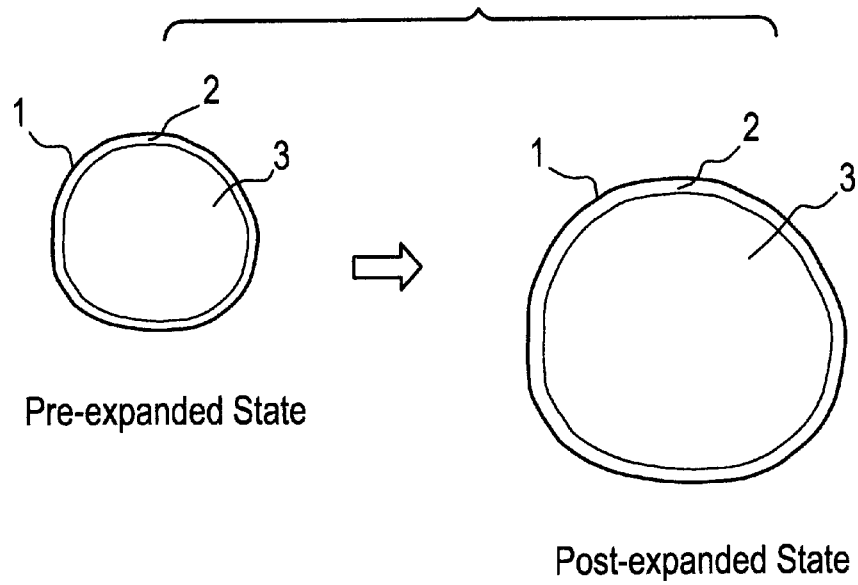
FIG. 1 illustrates one embodiment of a microballoon for use in the present invention.
Figure 3:
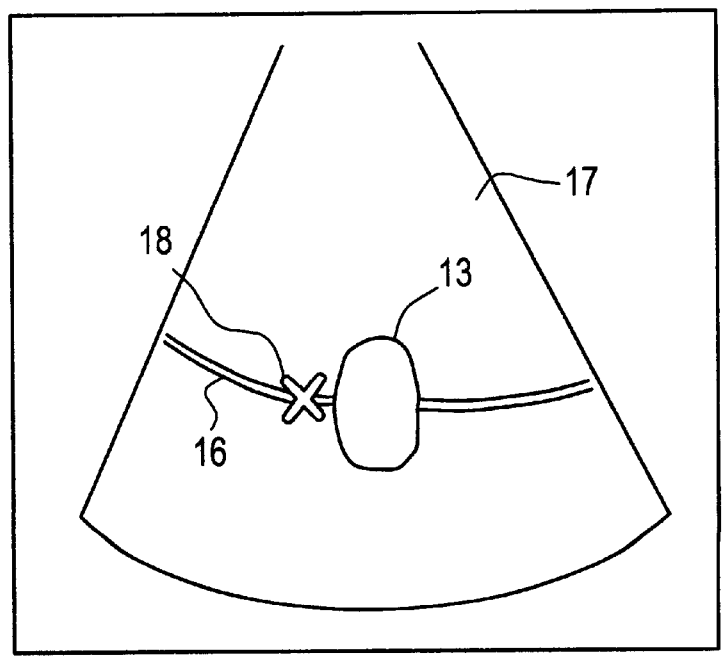
FIG. 3 illustrates an image displayed on a display section in the apparatus of the present invention.
Figure 2:
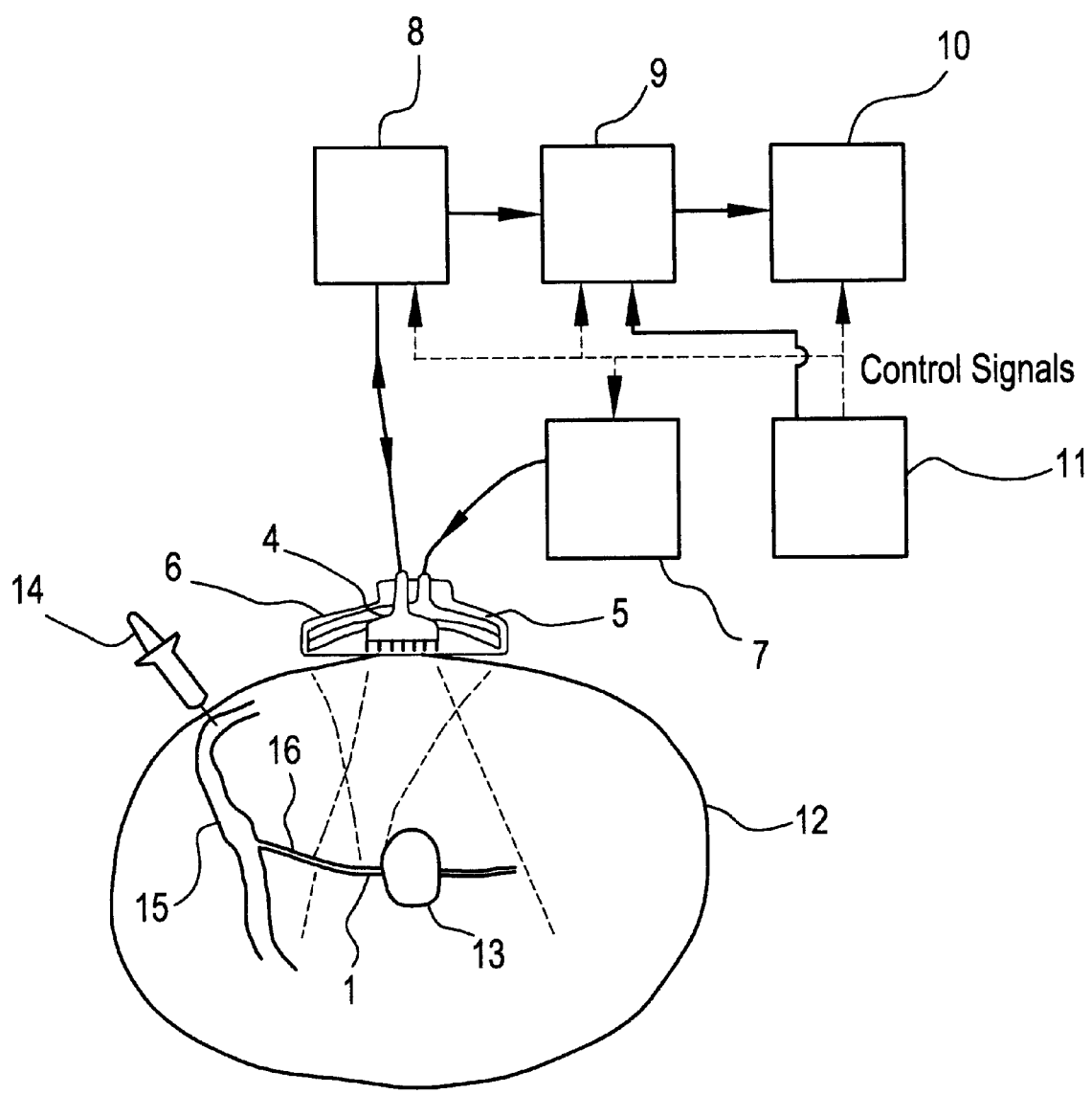
FIG. 2 illustrates an apparatus which can conduct the blood flow blocking method of the present invention.

FIG. 1 illustrates one embodiment of a microballoon for use in the present invention, FIG. 2 illustrates an apparatus which can conduct the blood flow blocking method of the present invention, and FIG. 3 illustrates an image displayed on a display section in the apparatus.

In FIG. 1, the microballoon 1 is shown in its pre-expanded state on the left and in its post-expanded state on the right. The microballoon 1 is formed by encapsulating a pressurized gas 3 within a shell 2. At ordinary temperature, the gas 3 in the microballoon 1 cannot escape from the shell 2 such as by bursting the shell 2. However, when the temperature of the gas 3 is increased close to the softening point temperature of the material constituting the shell 2, the gas 3 expands to push and enlarge the shell 2. For example, the microballoon 1 comprises a shell 2 of a polycaprolactone-type material, known by trade name "Celgreen," which has a softening point temperature of 42° C. and is biodegradable, and the material itself degrades to disappear within a few days—a few weeks in a living body. The time period needed for disappearance is set so that the expanded microballoon 1 endures longer than the time needed for the microballoon 1 to completely necrotize the target tissue and the expanded microballoon 1 disappears relatively shortly after the necrotization. Therefore, the disappearing time period is, for example, more than a few days and less than a few months. In other words, the disappearing time period can be considered as the lifetime of the microballoon. A microballoon having a lifetime of more than a few days and less than a few months is exemplified by one made of a polycaprolactone of a selected molecular weight.

FIG. 2 shows one example of an ultrasonic imaging apparatus which is suitable for conducting the invention method and has aiming means. In FIG. 2, the members designated by the reference numerals are as follows: 4) an imaging array transducer, 5) a high power irradiation focusing transducer, 6) a probe, 7) a high power transmitter section, 8) an ultrasound transceiver section, 9) and imaging section, 10) a display section, 11) a controller section, 12) a man, 13) a target region, 14) a microballoon injector, 15) a blood vessel, and 16) a capillary vessel. Parts the same as those shown in FIG. 1 are denoted by the same reference numerals.

The microballoon 1 is injected into the blood vessel 15 of the man 12 using the microballoon injector 14. (In practice, many microballoons 1 are injected at one time.) The probe 6 which comprises the imaging array transducer 4 and the high power irradiation focusing transducer 5 is used to take rough aim at the target region 13 within the man 12, and an ultrasonic receive signal received in this condition is used to obtain an ultrasonic image 17 (FIG. 3) via the ultrasound transceiver section 8 and the imaging section 9. On the display section 10, the ultrasonic image 17 is displayed with a mark 18 superimposed, indicating the focus location of the high power irradiation focusing transducer, as shown in FIG. 3. In FIG. 3, reference numeral 17 designates an ultrasonic image which represents a tomograph of the man, and numeral 18 designates a mark which indicates the focus location of the high power irradiation focusing transducer. An operator takes exact aim at the target region 13 while viewing the ultrasonic image 17 and the mark 18 displayed on the display section 10, and then conducts the operations for effecting the ultrasonic high power irradiation. The high power irradiation of the ultrasound warms the target region 13. Accordingly, the ultrasonic imaging apparatus shown in FIG. 2 represents one embodiment of the warming apparatus of the present invention.

Many widely different embodiments of the invention may be configured without departing from the spirit and the scope of the present invention. It should be understood that the present invention is not limited to the specific embodiments described in the specification, except as defined in the appended claims.

What is claimed is:

1. A blood flow blocking method which comprises the steps of:
    injecting microballoons into a blood flow system of a living body;
    expanding the microballoons by warming a predefined region of the body to increase temperature of the region; and
    choking capillary vessels of the body with the expanded microballoons.

2. A warming apparatus comprising:
    means for injecting microballoons into a blood flow system of
    a living body; and
    means for warming a predefined region of the body,
    the warming apparatus causing the expanding of the microballoons by increasing temperature of the microballoons and of the predefined region thereby to choke capillary vessels of the body with the expanded microballoons.

3. The warming apparatus of claim 2, wherein softening point temperature of a material of a shell constituting the microballoon is higher than ordinary temperature of the body and is lower than burn temperature of the body.

4. The warming apparatus of claim 2, wherein the warming means increases the temperature of the predefined region by transmitting focused ultrasound toward the predefined region.

5. A therapeutic apparatus comprising:
    means for placing microballoons into a living body; and
    means for controlling the temperature of a predetermined region of said living body to be within a predetermined temperature range by applying heat to at least said predetermined region to cause said microballoons caused to be disposed within said predetermined region of said living body to expand and thereby become stationary within the predetermined region of said body and thereby cause the heat applied to the predetermined region to be concentrated in the locality of the microballoons disposed in the predetermined region of the body.

6. The apparatus of claim 5, wherein softening point temperature of a material of a shell constituting the microballoon is higher than ordinary temperature of the body and is lower than burn temperature of the body.

7. The apparatus of claim 5, wherein the moans for controlling increases the temperature of the predetermined region by transmitting a focused ultrasound toward the predetermined region.

8. A method of applying heat to a predetermined region of a living body, comprising the steps of:
    injecting microballoons into a predetermined region of the body;
    applying heat to at least the predetermined region of the body, thereby to cause the microballoons disposed thereat to expand and thereby become stationary in the predetermined region of the body; and
    applying further heat to the predetermined region of the body to cause concentration of the heat, at the expanded microballoons so that the heat in the predetermined region of the body will be selectively controlled.

* * * * *